United States Patent [19]

Edoga

[11] Patent Number: 5,662,614
[45] Date of Patent: Sep. 2, 1997

[54] BALLOON EXPANDABLE UNIVERSAL ACCESS SHEATH

[76] Inventor: John K. Edoga, 10 Franklin Pl., Morristown, N.J. 07960

[21] Appl. No.: 437,393

[22] Filed: May 9, 1995

[51] Int. Cl.$^6$ .............................................. A61M 39/22
[52] U.S. Cl. ........................ 604/167; 604/248; 604/256; 604/171; 604/96; 606/198
[58] Field of Search ........................ 604/167, 164, 604/171, 96; 606/194, 198

[56] References Cited

U.S. PATENT DOCUMENTS

| | | | |
|---|---|---|---|
| 4,140,126 | 2/1979 | Choudhury | 128/325 |
| 4,577,631 | 3/1986 | Kreamer | 128/334 |
| 4,592,754 | 6/1986 | Gupte et al. | 623/4 |
| 4,617,932 | 10/1986 | Kornberg | 623/1 |
| 4,655,752 | 4/1987 | Honkanen et al. | 604/256 |
| 4,787,899 | 11/1988 | Lazarus | 623/1 |
| 4,820,298 | 4/1989 | Leveen et al. | 623/1 |
| 4,896,670 | 1/1990 | Crittenden | 606/194 |
| 5,037,392 | 8/1991 | Hillstead | 604/96 |
| 5,064,435 | 11/1991 | Porter | 606/198 |
| 5,078,720 | 1/1992 | Burton et al. | 606/108 |
| 5,104,399 | 4/1992 | Lazarus | 623/1 |
| 5,116,318 | 5/1992 | Hillstead | 604/96 |
| 5,116,365 | 5/1992 | Hillstead | 623/1 |
| 5,123,917 | 6/1992 | Lee | 623/1 |
| 5,192,297 | 3/1993 | Hull | 606/195 |
| 5,197,476 | 3/1993 | Nowacki et al. | 128/660.03 |
| 5,197,977 | 3/1993 | Hoffman, Jr. et al. | 623/1 |
| 5,202,757 | 4/1993 | Heyn et al. | 606/198 |
| 5,207,695 | 5/1993 | Trout, III | 606/153 |
| 5,211,658 | 5/1993 | Clouse | 623/1 |
| 5,211,683 | 5/1993 | Maginot | 623/1 |
| 5,219,355 | 6/1993 | Parodi et al. | 606/191 |
| 5,250,069 | 10/1993 | Nobuyoshi et al. | 606/192 |
| 5,250,070 | 10/1993 | Parodi | 606/194 |
| 5,263,932 | 11/1993 | Jang | 604/96 |
| 5,290,295 | 3/1994 | Querals et al. | 606/108 |
| 5,299,575 | 4/1994 | Sandridge | 606/108 |
| 5,316,023 | 5/1994 | Palmaz et al. | 606/198 |
| 5,330,528 | 7/1994 | Lazim | 606/194 |
| 5,334,142 | 8/1994 | Paradis | 604/53 |
| 5,342,387 | 8/1994 | Summers | 606/198 |
| 5,354,308 | 10/1994 | Simon et al. | 606/198 |
| 5,360,443 | 11/1994 | Barone et al. | 623/1 |
| 5,370,683 | 12/1994 | Fontaine | 606/198 |
| 5,382,261 | 1/1995 | Palmaz | 606/158 |
| 5,456,694 | 10/1995 | Marin et al. | 606/198 |
| 5,484,418 | 1/1996 | Quiachon et al. | 604/167 |
| 5,507,767 | 4/1996 | Maeda et al. | 606/198 |
| 5,507,769 | 4/1996 | Marin et al. | 606/198 |

FOREIGN PATENT DOCUMENTS

| | | |
|---|---|---|
| 0461791 | 6/1991 | European Pat. Off. . |
| 0556850 | 2/1993 | European Pat. Off. . |
| 9300867 | 1/1993 | WIPO . |

OTHER PUBLICATIONS

"Guidelines for development and use of transluminally palced endovascular prosthetic grafts in the arterial system", Journal of Vascular Surgery, vol. 21, No. 4, pp. 670–685 (Apr. 1995).

"Cardiovascular Devices and the Food and Drug Administration", Circulation, vol. 89, No. 4, pp. 1903–1904 (Apr. 1994).

"The Role of Clinical Trials in the Food and Drug Administration Approval Process for Cardiovascular Devices", Circulation, vol. 89, No. 4, pp. 1900–1902 (Apr. 1994).

*Primary Examiner*—Sam Rimell
*Assistant Examiner*—Robert V. Racunas
*Attorney, Agent, or Firm*—Lerner, David, Littenberg, Krumholz & Mentlik

[57] ABSTRACT

The present invention relates to a balloon expandable universal access sheath which can be used in surgical procedures such as abdominal aortic grafting. The device allows for great surgical flexibility, ease of insertion and, in addition, the ability to collect and recirculate blood.

5 Claims, 13 Drawing Sheets

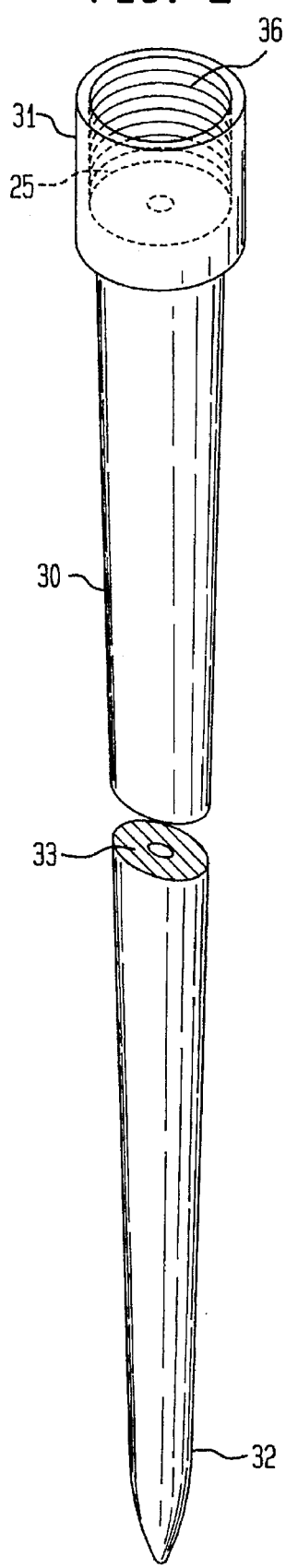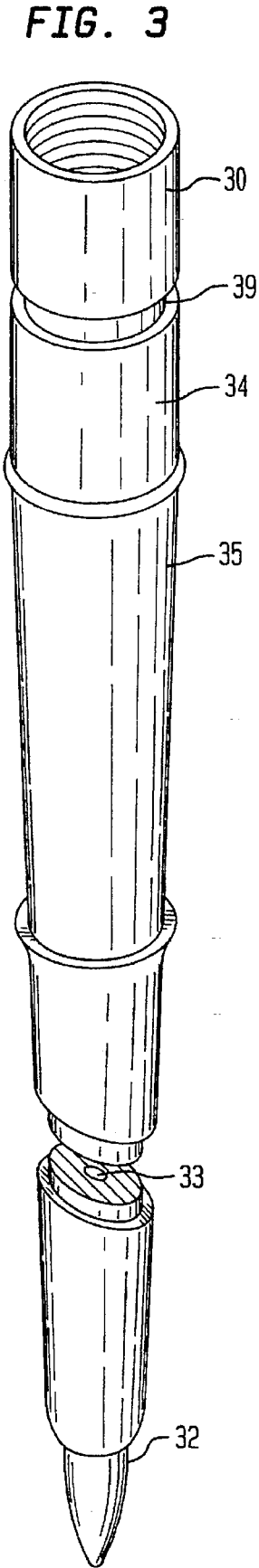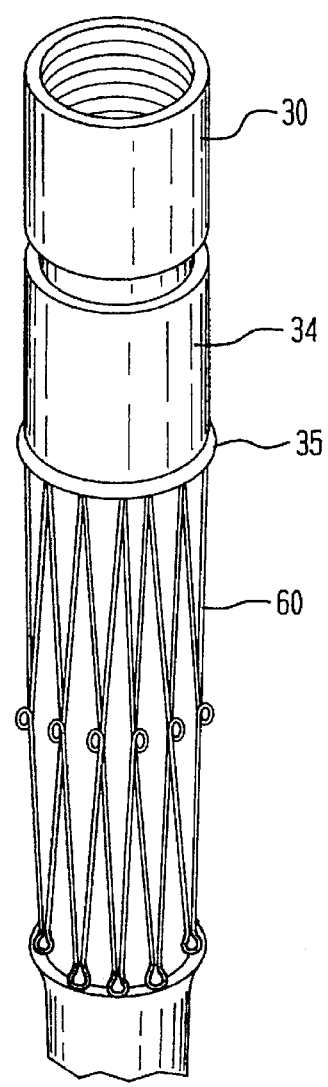

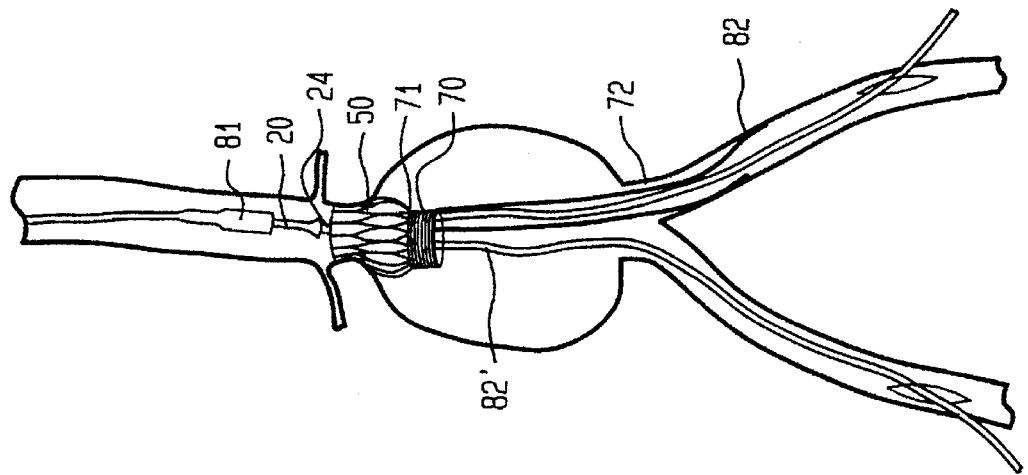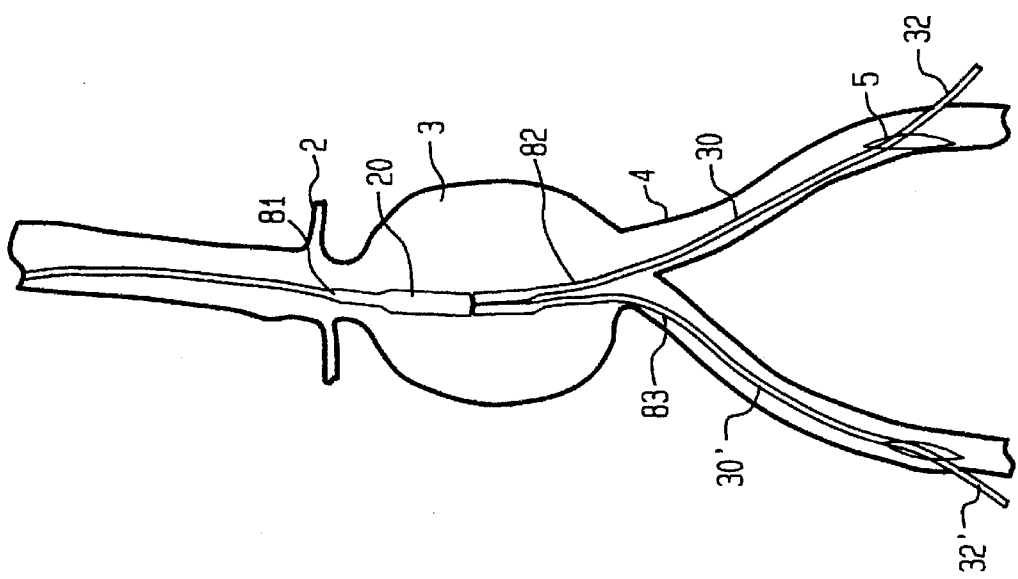

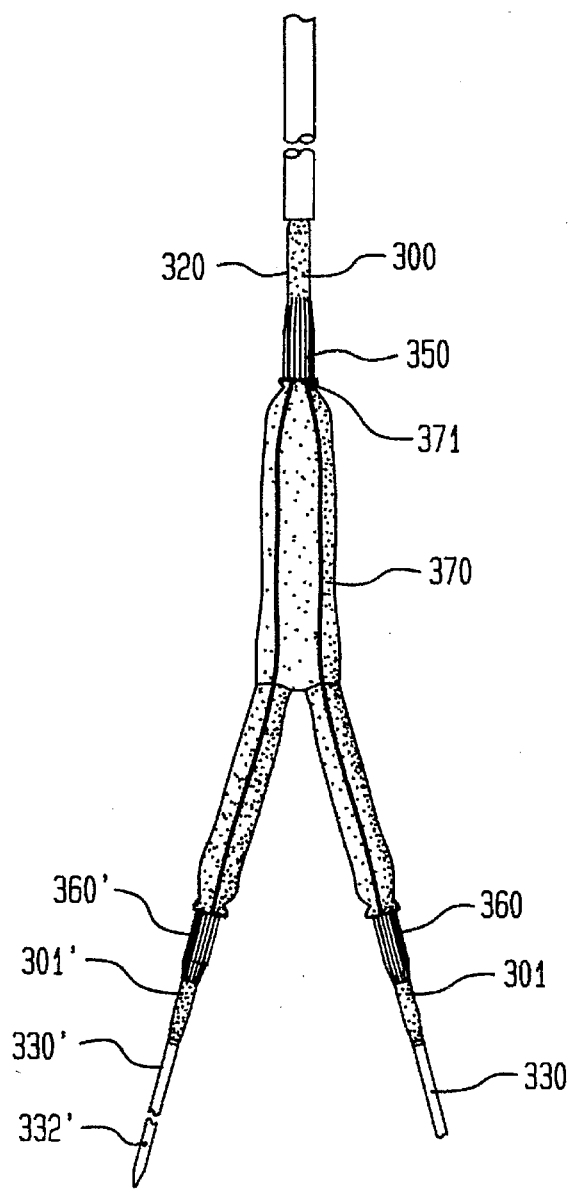
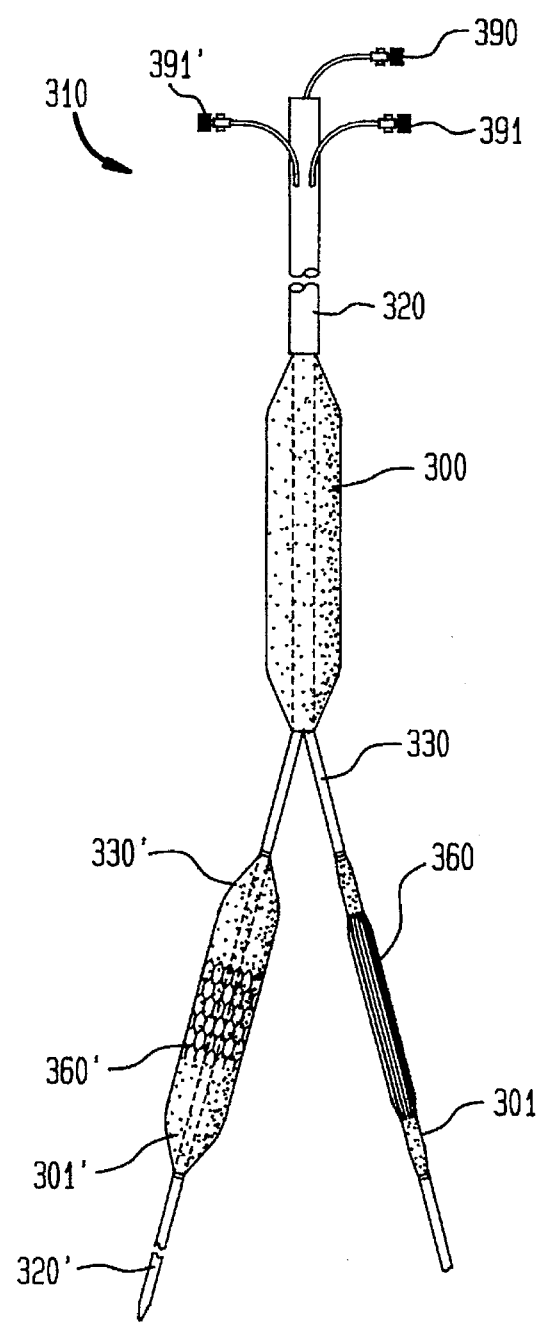
FIG. 11
FIG. 12

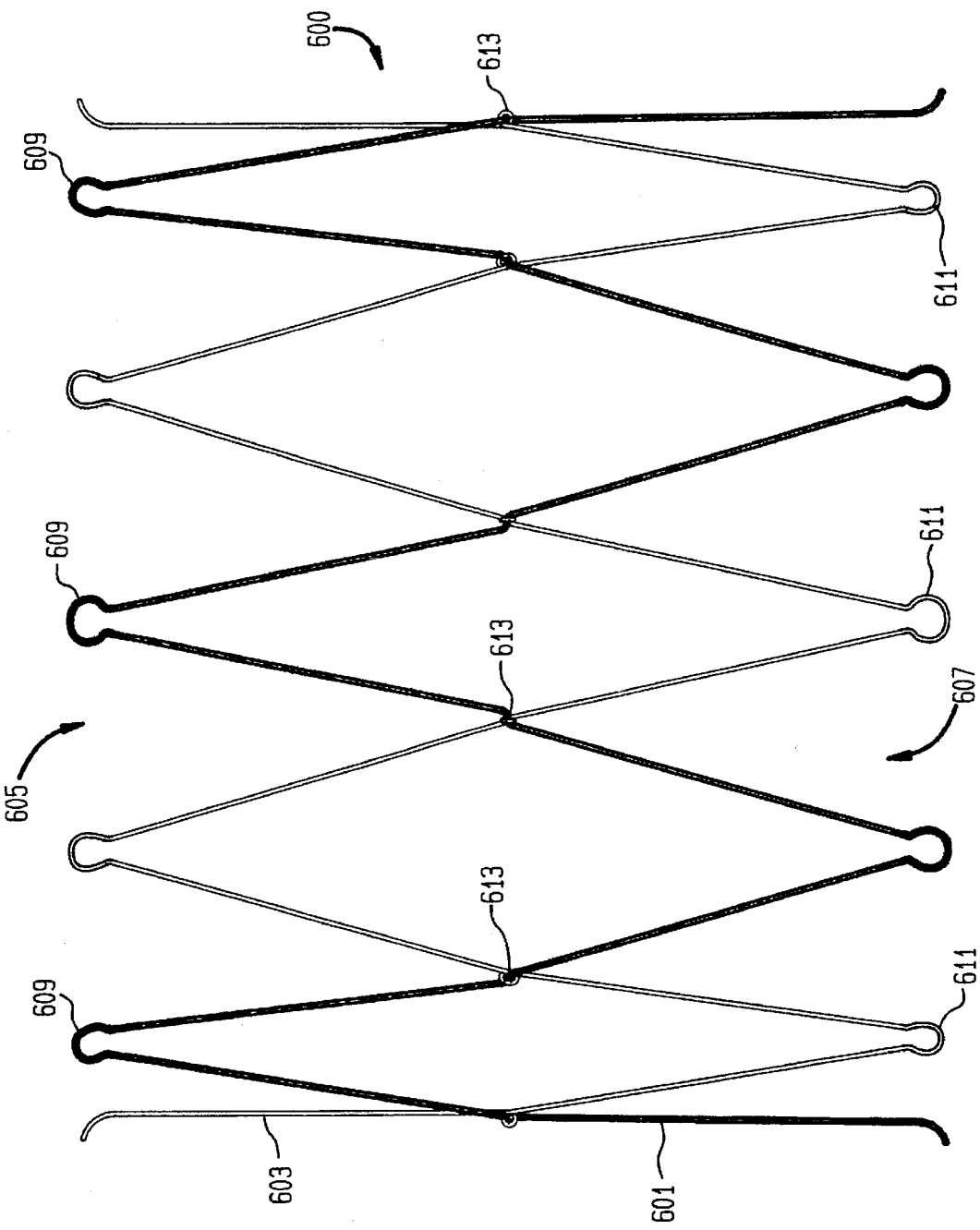

BALLOON EXPANDABLE UNIVERSAL ACCESS SHEATH

FIELD OF THE INVENTION

The present invention relates to the field of surgical and, in particular, endo-vascular surgery, and specifically devices which are useful for introduction or access ports.

BACKGROUND OF THE INVENTION

There are several medical conditions which currently require surgery and/or the use of an abdominal aortic graft. These conditions include: abdominal aortic aneurysms, aortic and iliac occlusive disease following balloon angioplasty and aorta-distal arterial embolization. Each of these conditions most commonly affects the aorta immediately below the take off or junction with the renal arteries through and including the area where the aorta divides into the common iliac arteries.

For illustrative purposes, consider a patient having an abdominal aortic aneurysm. An aneurysm is defined as a sac formed by localized dilatation of the aorta. Aneurysms can lead to occlusion and more notably rupture of the arterial wall and thus unconfined bleeding into the abdomen. If left untreated, the patient may die of internal bleeding.

One method of treating this disorder is through the use of an arterial replacement. However, even though the mortality rate for elective aneurysm resection is usually less than 5%, the morbidity of the needed surgery is quite severe. The average hospital stay is ten to fourteen days at a total cost of tens of thousands of dollars. For ruptured aneurysms, the hospital mortality rate is approximately 75% with greater than ⅔ of the deaths occurring during surgery or within a few hours after surgery. For survivors, the morbidity includes limb and bowel loss and renal failure requiring life long dialysis. When an aortic aneurysm ruptures, resource consumption rises astronomically. There are also a great number of patients in whom co-morbid factors constitute relative or absolute contraindications to this type of surgery such as patients with severe coronary artery disease or pulmonary insufficiency.

Another technique involves the insertion of a graft of material within the existing aorta and anchoring the graft in place such that it acts to carry blood through the afflicted portion of the aorta. This is analogous to fixing a leaking pipe by placing another pipe of smaller diameter within the existing pipe and, in essence, bypassing the afflicted area of the aorta. However, the technique does have some problems, including difficulty in accurately sizing and delivering the graft in a bifurcated blood vessel. One problem, for example, is that until surgery begins, it is often difficult to know exactly the length of a graft which will actually be required to reach from the affected area of the aorta just below the renal arteries down to and through the iliac arteries. While surgeons can estimate the necessary length, a graft which is too long may buckle or kink once flow is restored. If, on the other hand, the graft is too short then when a stent is released to anchor the graft in place, it may expand in an already weakened portion of the aortic or iliac arteries and cause rupture, leakage or other complications.

Perhaps the biggest problem, however, is getting both of the lower or iliac ends of the graft, which are to be disposed in the right and left iliac arteries, properly aligned and positioned while, at the same time, controlling the placement of the upper or aortic end of the graft. While a number of techniques have been suggested, the most common techniques use two guide wires which are inserted through the common femoral artery of one leg up into the body. A first guide wire is inserted through the common femoral artery in one leg such that its free end dangles in the aorta around the junction with the renal arteries. The other guide wire is fed in through the same leg and crosses over from one iliac artery into the other iliac artery and out through an incision in the common femoral artery of the other leg. See, for example, FIGS. 9 through 12, and the accompanying text of Baron et al., U.S. Pat. No. 5,360,443. The loose guide wire is used to guide the entire stent and graft assembly into the abdominal aorta above the iliac divide. The aortic or proximal end of the graft is exclusively fed through the femoral artery with the two iliac ends of the graft trailing behind. Thereafter, the second guide wire, which is looped up through both iliac ends of the graft, is used to help try to position the crossover iliac end into proper position in the iliac artery of the other leg. Beside the obvious difficulties in maneuvering the device, it is difficult to ensure that the graft does not become twisted and blocked during deployment. It is also difficult to control the placement of, in particular, the iliac portion of the graft which is being maneuvered into the non-insertion iliac artery.

Baron et al. also discloses insertion of an apparatus intraluminally to the aorta and in particular, to a ruptured aneurysm, through the axillary artery in the patients arm. See, for example FIGS. 13 and 14. However, this method and device appear limited to use in connection with ruptured aneurysms and Baron, et al. does not disclose the ability to accommodate a bifurcated graft.

Palmaz, et al., U.S. Pat. No. 5,316,022 disclosing inserting two individual grafts, rather than one bifurcated graft, through the individual femoral and iliac arteries up into the aorta. This leads to uniform sacrifice of the internal iliac circulation and would only be feasible in patients in whom both internal iliac arteries are already occluded. Also, the proximal end of the double individual graft stents will not, in all likelihood, produce a complete seal.

SUMMARY OF THE INVENTION

The present invention relates to an entry device which may be used in accordance with the surgical methods and devices described herein and, indeed, any form of endo-vascular surgery. The device allows for quick and easy deployment of other devices into blood vessels, retards bleeding and provides for collection of blood which may accumulate during surgery for return to the patient.

In accordance with one aspect of the present invention, there is provided an apparatus for introducing second apparatus into the body of a patient and for collecting blood. The apparatus includes a hollow sheath having a longitudinal axis extending between a first and second end, a hollow housing defining a housing chamber communicating with the first end of the hollow sheath and a first valve means disposed within the housing chamber. The first valve means for allowing insertion of the second apparatus into the housing chamber and through the sheath but substantially retarding blood from exiting the housing chamber. In a particularly preferred aspect, a blood removal means is connected to the housing chamber for removing blood from the housing chamber.

Methods of using this device are also contemplated.

BRIEF DESCRIPTION OF THE DRAWINGS

FIG. 2 is a view of a threaded lower or iliac mandril assembly.

FIG. 3 is a view of the mandril assembly of FIG. 2 further comprising a housing and a recess for retaining a stent.

FIG. 4 is a view of the mandril of FIG. 3 further illustrating a self-expanding stent.

FIG. 9 illustrates the final placement of a bifurcated mandril in accordance with the present invention in the area of aneurysm.

FIG. 10 illustrates the deployment of the aortic stent.

FIG. 11 illustrates a bifurcated mandril for delivering a bifurcated graft including balloon expandable stents.

FIG. 12 is a view of the bifurcated mandril of FIG. 11 illustrating the expansion of balloons and the expansion of a balloon expandable stent.

FIG. 16 is an illustration of a self-expanding stent.

DETAILED DESCRIPTION OF THE PREFERRED EMBODIMENT

Figure 1:
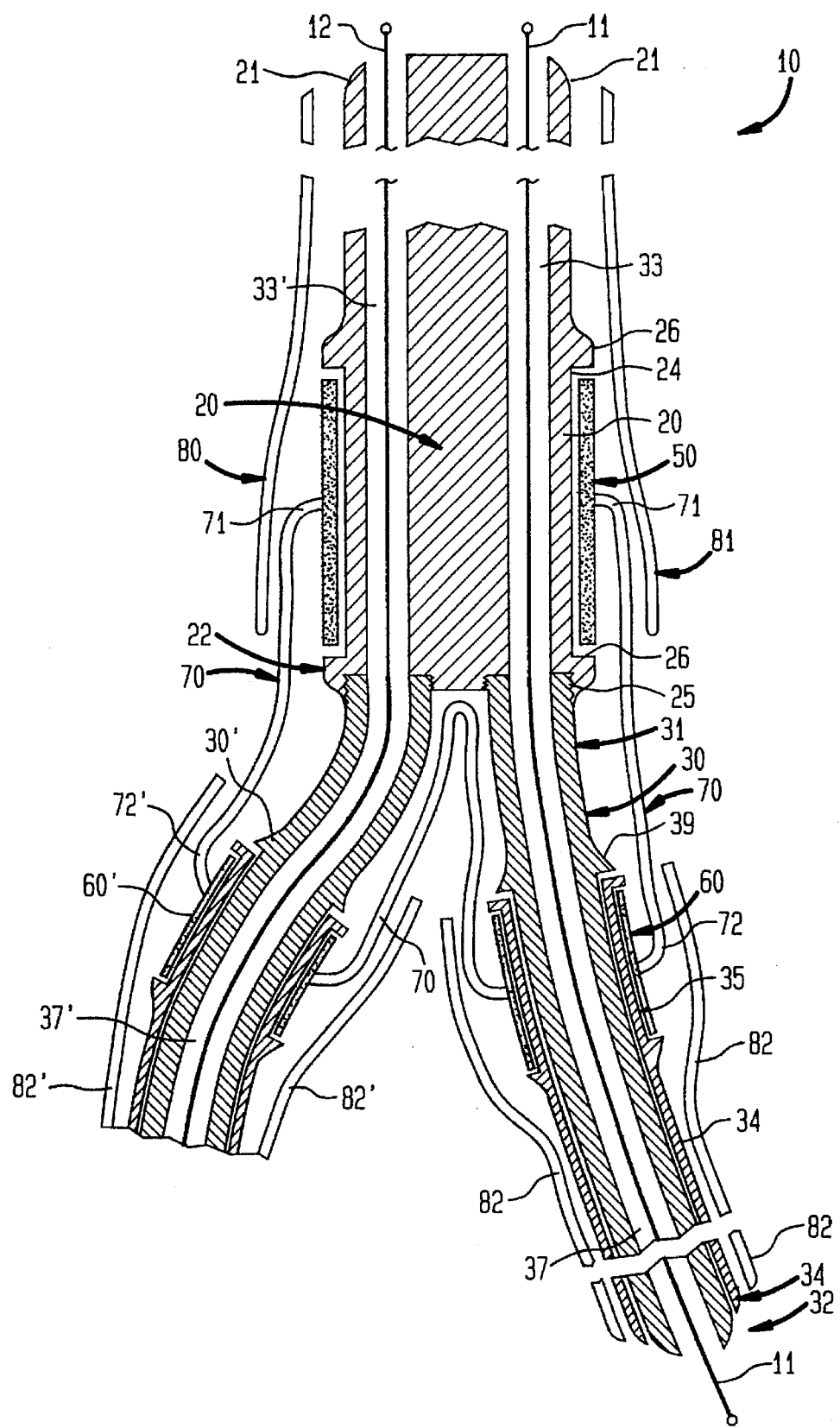
FIG. 1 is a cross-sectional view of a bifurcated mandril assembly in accordance with the present invention including a bifurcated graft which is retained by a plurality of sheaths.

In accordance with one preferred embodiment of the present invention, a graft carrying assembly is used to carry a bifurcated graft to an aneurysm. FIG. 1, which along with the other figures is not to scale, illustrates one graft carrying mandril assembly 10 in accordance with the present invention.

Assembly 10 is intended for insertion into a patient, and the elements of assembly 10 are generally described as being "proximal" or "distal" depending on their relative position with respect to the head and feet of the patient. When a member is referred to as having a "proximal" or "upper" portion and a "distal" or "lower" portion, the "proximal" or "upper" portion shall generally refer to the portion closest to patient's head and the "distal" or "lower" portion shall generally refer to the portion closest to the patient's feet. Referring to elements as being "proximal", "distal", etc. is for ease of reference purposes only, and should not be construed as requiring a specific location or direction with respect to the position of the patient's body.

Assembly 10 includes upper mandril 20, and two lower mandrils 30, 30'. Upper mandril 20 is generally cylindrical, and extends from a proximal end 21 to a distal end 22. The upper mandril also has two channels 33, 33' extending from the proximal end to the distal end, and the channels are sufficiently large enough to accept guide wires 11, 12 respectively. Although not shown, a single channel large enough to accommodate both wires may also be used. The upper mandril 20 also has a recess 24 which extends around the outer surface of the mandril. The recess holds a cylindrical self-actuating or self expandable aortic stent 50, and the edges 26 of recess 24 prevent the axial movement of the stent, i.e. movement parallel to the longitudinal axis of the mandril.

At the distal end 22 of mandril 20 are means 25 for detachably coupling lower mandril 30 to upper mandril 20. In the preferred embodiment of FIG. 1, coupling means 25 comprises screw threads on the outer surface of the proximal end 31 of lower mandril 30, and cooperating threads in channel 33 at the distal end 22 of upper mandril 20. However, any arrangement which can allow for the detachable coupling of the upper mandril 20 and lower mandril 30 is structurally acceptable. For example, detachable coupling means 25 may also include a different threaded assembly, a detachable pressure coupling, a slidable coupling member, a series of perforations, or other similar means.

Lower mandril 30 also includes a hollow channel 37 extending from its proximal end 31 to distal end 32. Lower mandril 30 is generally cylindrical, but preferably narrower in diameter than upper mandril 20. Channel 37 is cooperatively disposed relative to channel 33 of the upper mandril such that upon exiting channel 33 of upper mandril 20, guide wire 11 passes into and through channel 37. A housing 34 is disposed on the outer surface of the lower mandril, and extends from raised edge 39 below the proximal end 31 until near the distal end 32. Housing 34 is preferably fixed in place such that it is not capable of axial movement with respect to the length of mandril 30, but is freely rotatable about the mandril's longitudinal axis. In other words, the housing 30 cannot move up and down the mandril, but can rotate about it. Housing 30 also defines a recess 35 on its outer surface for holding a self-actuating or self expanding cylindrical iliac stent 60.

Another lower mandril 30' is also detachably engaged with the distal end 22 of the upper mandril. Lower mandril 30' has the same structure as lower mandril 30, including a channel for accepting guide wire 12, and a rotatable housing with a recess for holding an iliac stent 60'.

FIGS. 2-4 offer a perspective view of alternative lower mandrils with a somewhat different coupling structure than the lower mandril shown in FIG. 1. FIG. 2 shows a mandril 30 with channel 33 through which a guide wire may be passed. However, FIG. 2 also shows an alternative coupling means 25 whereby the threaded receiving member of the lower mandril has a wider inside diameter than the corresponding threaded member at distal end 22 of upper mandril 20. FIG. 3 illustrates the same alternative lower mandril 30 but contained in housing member 34. The housing member 34 starts at raised edge 39 and ends at or near the distal end 32 and is freely rotatable around mandril 30. As shown in FIG. 4, iliac stent 60 is disposed and retained in recess 35.

The actual distance between the proximal ends and distal ends of the various mandrils or members are preferably quite large compared to the mandrils' diameter. For example, the length of upper mandril 20 may be 100 cm while the diameter is 5 mm. All of the mandrils should be of a material sufficiently flexible for being threaded through the arteries of a patient, such as hollow, helically coiled wire or molded plastic.

As shown in FIG. 1, a bifurcated graft 70 is attached to stents 50, 60, and 60'. The graft is pant-shaped or "Y" shaped having an open proximal or aortic end 71 and two open distal or iliac ends 72,72'. Proximal end 71 is preferably attached midway between the ends of aortic stent 50 in nearly any manner known in the art. Preferably, the graft is sutured to the stents, using for example, interrupted, non-absorbable sutures. Each distal end 72,72' of the graft 70 is attached midway between the ends of the corresponding iliac stents 60,60' of lower mandrils 30,31'. In other words, the Y-shaped graft 70 is fitted over assembly 10 at the junction between the upper mandril and the lower mandrils and is attached at its ends to the middle of the stents.

A wide variety of stents are known and can be used. In such cases, the graft 70 may not be attached to the stents in the manner just described. Rather, attachment will be dictated by the stent itself.

A number of commercially available bifurcated grafts 70 may be used. For example, the Bard Velex graft available from C. R. Bard, Inc. may be used. A thinner version of such a graft could also be used as the graft is being used endo-luminally i.e. inserted within an already existing vessel. Also, an expandable PTFE graft manufactured by Impra of Scottsdale, Ariz. may be used. When PTFE is used, and, in particular, where an adjustable length graft will be used, the graft must be designed to accommodate stretching. Preferably, graft 70 is adjustable in terms of length. Specifically, the iliac and/or aortic portion of the graft may be constructed using accordion-type folds or pleats (crimped) which, when pulled, will expand allowing for the adjustment of the length of the graft and, in particular, the placement of the iliac stents. The actual size of the graft is chosen by the surgeon based on the particular needs of the patient. For example, a 16×8 graft 70 will have a 16 millimeter opening at upper end 71 and 8 millimeter openings at distal ends 72,72'. The graft 70 itself is made of a flexible material which may stretch to accommodate vessel growth, and/or to allow the graft to be used over a wide range of lengths.

The assembly 10, including the graft 70, is then encased in a removable sheath. The sheath may be a single integral unit, but is preferably three separate sheaths 81,82,82', covering the stents on the upper mandril and the lower mandrils, respectively. Sheath 81 extends from approximately the proximal end 21 of upper mandril 20 to the distal end 22. Likewise, sheaths 82,82' extend from approximately the proximal ends of lower mandrils 30,30' to the distal ends of the lower mandrils. The sheaths are sized to tightly fit over the mandrils, stents and graft to prevent the stents from expanding.

In operation, the device just described may be used as follows. First, the patient is prepped from neck to knees and draped in a fashion to expose the left of the neck above the clavicle and both groins. The patient is laid supine with the neck hyper-extended and turned to the right. General or local anesthetic, the latter with a sedative, may be administered.

Figure 7:
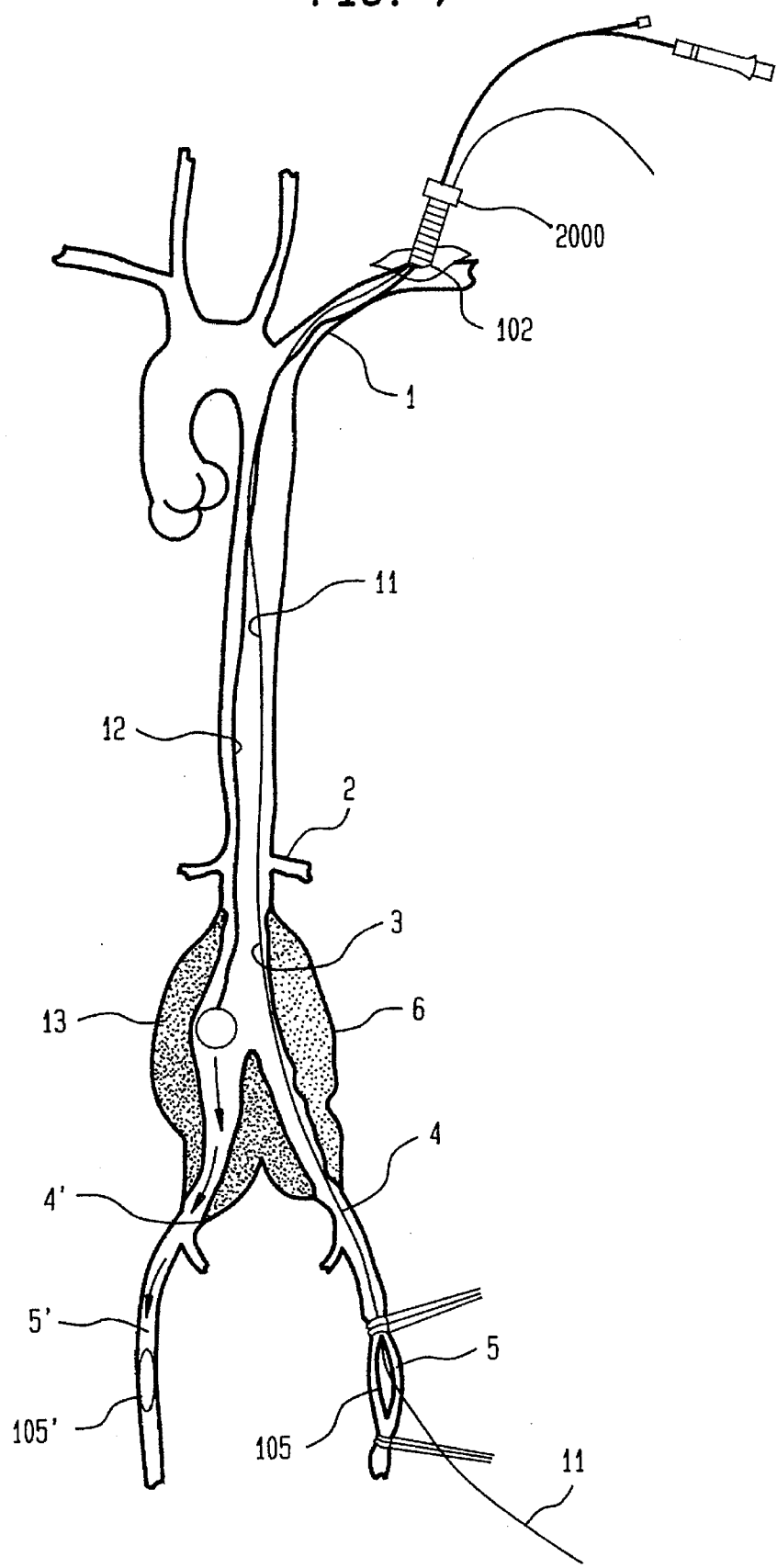
FIG. 7 is a view of an aneurysmal aorta illustrating the insertion of guide wires through a balloon expandable universal access sheath.
Figure 8:
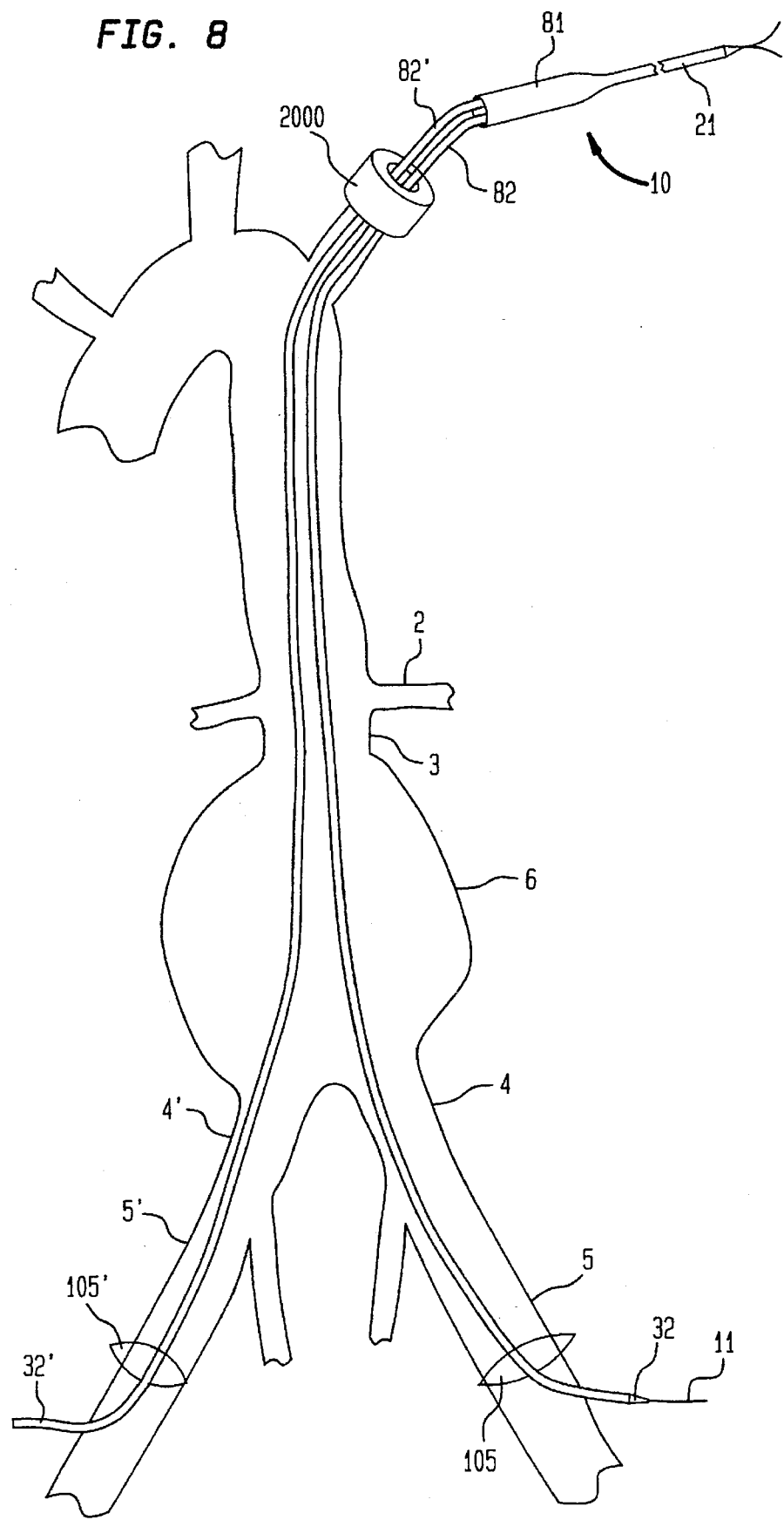
FIG. 8 illustrates the insertion of a bifurcated mandril assembly over guide wires.

As shown in FIGS. 7 and 8, a transverse skin incision is made above the left clavicle and the lateral third of the left sternocleidomastoid muscle is divided and retracted medially. The internal jugular vein is also retracted medially exposing the scalenus anticus muscle. The phrenic nerve runs along the antero-lateral border of the scalenus anticus muscle and injury must be avoided during the procedure. The scalenus anticus muscle is then divided to expose the subclavian artery 1 (and specifically, the supraclavicular left subclavian artery). The subclavian artery 1 is encircled and mobilized circumferentially, taking care not to enter the pleural cavity. The branches of the subclavian artery are controlled with loops of 2-0 silk.

Longitudinal incisions are then made in both femoral regions. The common femorals 5,5', the superficial femoral and the profounda femoris arteries in both groin regions are isolated and controlled with vessel loops. The common femoral arteries 5,5' are mobilized circumferentially as high as possible into the region of the iliac arteries 4,4' and any tortusity is straightened out by this dissection.

Figure 18:
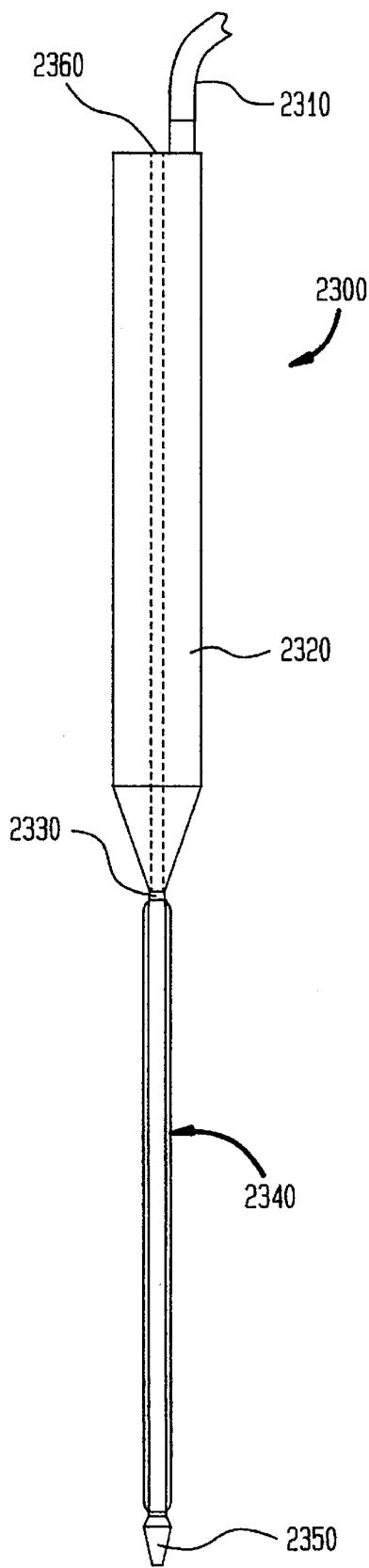
FIG. 18 is a view, in partial cross-section, of a balloon inflation device for use in conjunction with a balloon expandable access sheath.
Figure 17:
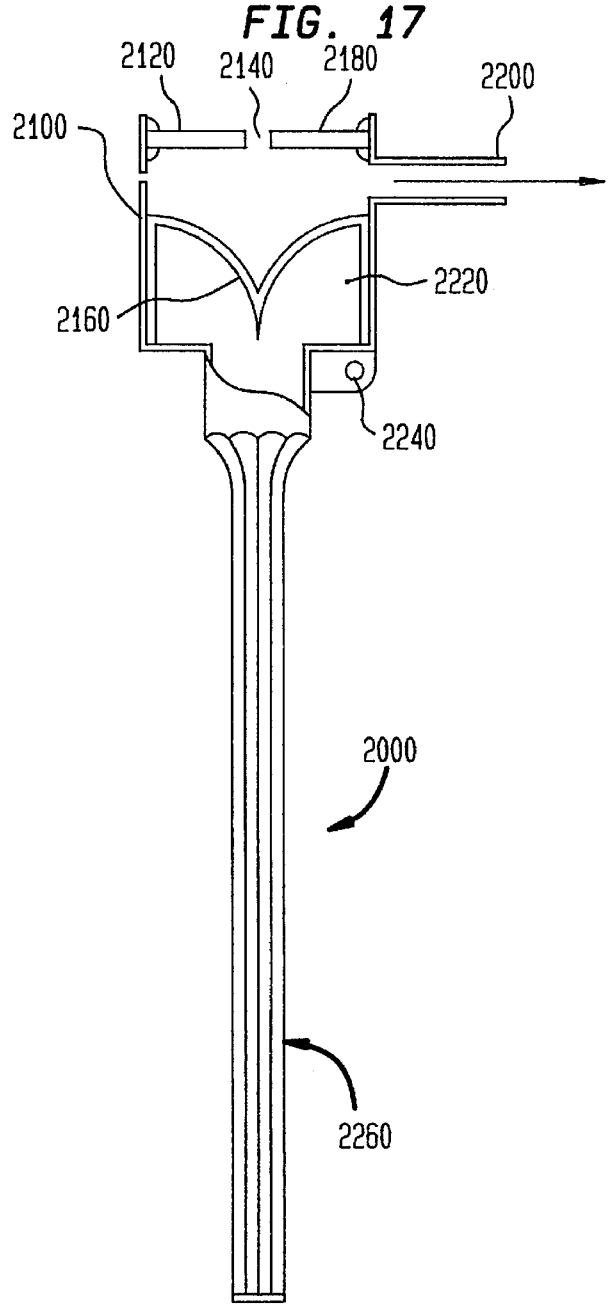
FIG. 17 is a view, in partial cross-section, of a balloon expandable universal access sheath.

As illustrated in FIGS. 7 and 8, a puncture is made into the subclavian 1 and a Balloon Expandable Universal Access Sheath ("BEUAS") 2000 or some other, conventional, access port is inserted (the BEUAS 2000 is illustrated in FIGS. 17 and 18). A large bolus of Heprin is given. A first guide wire 11 is then inserted through the BEUAS. Although the guide wire may be guided through the body with a guide catheter, the wire is preferably passed within a floatation catheter 13. The use of a flotation catheter takes advantage of blood flow for placement and minimizes the contact between the guide wire and the arterier wall. Guide wire 11 is fed down through subclavian 1, past renal arteries 2, through the abdominal aorta 3 and past the aneurysm 6 to be treated, into and through iliac artery 4, and finally out a small transverse arteriotomy 105 made in the common femoral artery 5 of the patient's leg. Likewise, a second guide wire 12 is fed into the subclavian 1 and out another incision 105' in the common femoral artery 5' of the other leg.

Thus, the free ends of both guide wires 11, 12 protrude from the patient's body, one end of each wire protruding from each leg and the other ends both protruding from the subclavian. Sufficient wire 11, 12 is left protruding from the body to allow for easy manipulation. The guide wires 11, 12 may be as much as 12 feet in length, or even longer. Specifically, the guide wire should be sufficiently long to allow for cbntrol of both ends to be maintained, even when the graft is put into place. As will be self-evident, once the graft is in position in the aorta, for example, its distal mandrils will extend from the patient a considerable number of feet. Therefore, to maintain firm control over the system, the guide wire must be sufficiently long to accommodate and allow access thereto even when the full length of the mandril is exposed through the patient's legs.

The portions of wires 11,12 extending out of subclavian 1 are then fed into and through the appropriate channels 37, 37' of the lower mandrils and then channels 33, 33' of the upper mandril. (see FIG. 1). Once the assembly 10 has been placed on the guide wires, the two distal ends 32,32' of the sheathed assembly 10 are inserted into the subclavian 1 through the BEUAS 2000 and fed through the patient's body until the ends 32,32' protrude from the incisions in the common femorai arteries 5,5' (FIGS. 8–9). Alternatively, the assembly can be releasably attached to the guide wires 11, 12 such that the assembly can be pulled into place by pulling on the guide wires. This can be accomplished by some type of stop placed on the guide wires above the assembly 10 threaded thereon which will engage the proximal end 20 of the assembly 10. When the wires 11, 12 are pulled through the femoral arteries 5, 5', the stops will engage the assembly 10 and pull it into place.

As soon as the ends of the mandrils protrude from the body, the graft 70 is ready to be introduced into the body and positioned. Graft 70 in combination with the mandril assembly 10 are advanced along guide wires 11,12 and moved to aneurysm 6 by manipulating the protruding portions of the mandrils, i.e. by pulling and pushing on lower ends 32, 32' and upper end 21 (FIG. 9). While feeding the graft through the patient, care must be taken to ensure the sheaths 81, 82, 82' remain in place in order to prevent premature deployment of the stents.

The graft is correctly positioned within the aneurysm 6 when the aortic stent 50 is in position below the junction with the renal arteries 2 (FIG. 9). When the graft is finally positioned, the graft and stents will be completely within the patient's body, while portions of the guide wires 11, 12, mandrils 20, 30, 30', housing 34, 34' and sheaths 81, 82, 82' will all extend out of the patient. The position of the graft 70 can be confirmed by reference to an angiogram which is taken using a pigtail catheter and an operating table having a radio-opaque ruler at the beginning of the procedure.

The graft is deployed by removing the individual sheaths. Once aortic end 71 of the graft 70 is in position, the aortic stent 50 is deployed by removing the sheath 81 by pulling the sheath back through the subclavian artery 1 (FIG. 10). Although the sheath 81 is tightly disposed around the graft 70 and upper mandril 20, it is not so tight that it can not be pulled off the upper mandril, especially when the lower mandrils 30 are held in place. As shown in FIG. 10, once the sheath 81 is pulled off graft 70, the self-actuating stent 50 will expand out of recess 24 and push the proximal end 71 of the graft against the walls of the aorta 3 above the aneurysm 6. This fixes the upper end 71 of the graft 70 into place in the aorta 3.

Next, the lower mandrils 30 are detached from the upper mandril 20. For example, in accordance with the preferred embodiment shown in FIG. 1, the upper end 21 of the upper mandril 20 and the housing 34 of the lower mandril 30 are grasped and prevented from rotating. Next, lower mandril 30 is rotated by rotating the lower end 32. By rotating lower mandril 30 while upper mandril 20 is kept in place, the screw coupling 25 will come undone and the lower mandril will be detached from the upper mandril. Further, because housing 34 is prevented from rotating, the lower mandril 30 will be able to spin within housing 34 without twisting the iliac leg of the graft 70, stent 60 or sheath 82.

Once the lower mandril 30 is detached from the upper mandril assembly, the lower mandril is manipulated to a position such that the lower end 72 of graft 70 is the correct position within iliac artery 4. In other words, the graft 70 is pulled and stretched to the appropriate length. Once in position, the housings 34 and mandril 30 are kept steady while sheath 82 is retracted through the common femoral artery, thereby deploying the iliac stent 60 and fixing the distal end 72 of graft 70 in place in iliac artery 4. For accuracy and simplicity, usually the two legs are done sequentially. For example, the other iliac stent is deployed in the other leg in the same manner described in connection with the foregoing stent.

It may also be desirable to include within those portions of the distal and proximal mandrils which remain exposed from the patient's body, a structure which helps prevent the premature deployment of stents 50, 60, 60' by inadvertent removal of sheaths 81, 82 and 82. This can be accomplished by the use of a collapsible structure at each end of the mandril assembly which will protrude from the patients body. The structure stretches the sheath in the localized area thereof making it difficult to move the sheath axially relative to the housing, mandril and/or other structures. Therefore, the surgeon can grip the entire assembly, including the sheath, between that structure and the outer-most end of the mandril, without significant fear of inadvertently deploying the stent covered by that sheath. If, as is preferred, the sheath is made of a more rigid, slick, plastic material, then the assembly can be gripped above this structure without fear of inadvertent stent deployment as well. To deploy the stent either the sheath can be gripped above this structure and/or the device can be compressed or collapsed such that it no longer provides additional resistance. The structure could be a retaining band, a collapsible balloon, a spring loaded bearing or pad, a hook or latch, and the like.

Following the deployment of the right and left iliac portions of the graft 70, the various portions of the lower mandrils 30, 30' and housings 34, 34' are withdrawn through the femoral incisions and the upper mandril 20 is removed through the subclavian artery. Following the surgical procedures, a pigtail catheter is once again inserted into the surgical region to give a completion arteriogram. The guide wires 11, 12 are also removed. If satisfactory, each leg is flushed and femoral blood flow is restored after the arteriotomics are closed. The incisions are then closed and the wounds dressed.

A variety, of advantageous alternatives to the preferred embodiment described above are also possible. In the preferred embodiment above, the housing 34 was allowed to freely rotate relative to the lower mandril 30 in order to allow the mandril 30 to be unscrewed without effecting the position of the housing 34 and, therefore, causing a twisting of the graft 70. If some other form of detachment means is used, it may not be necessary to include an independently rotatable housing 34. For example, if the lower mandrils 30, 30' are connected to the upper mandril 20 by a microperforation or by some form of pressure or snap coupling, then it may be possible to build the housing 34 and/or the recess 35 into the mandril 30 per se.

In addition, guide wires 11, 12 could be eliminated by designing systems such that mandrils 20 and 30 are sufficiently long, sufficiently rigid, and sufficiently tapered so as to allow insertion directly through the subclavian 1 down into the aorta 3, through the iliac arteries 4 and out through the femoral arteries 5. In other words, rather than guiding the assembly through the body on a track of guide wires, long wiry mandrils themselves are used. Otherwise, however, the device can remain substantially unchanged. Such a system may be smaller than the embodiment shown in FIG. 1 by eliminating channels 33, 33', 37, 37'. A small upper mandril diameter may help reduce surgical trauma.

It is also possible to construct a hybrid device where a guide wire is permanently embedded in the mandril to provide a sufficient degree of rigidity and flexibility to allow the mandril to be properly placed with as little stress as possible upon the blood vessels.

Figure 5:
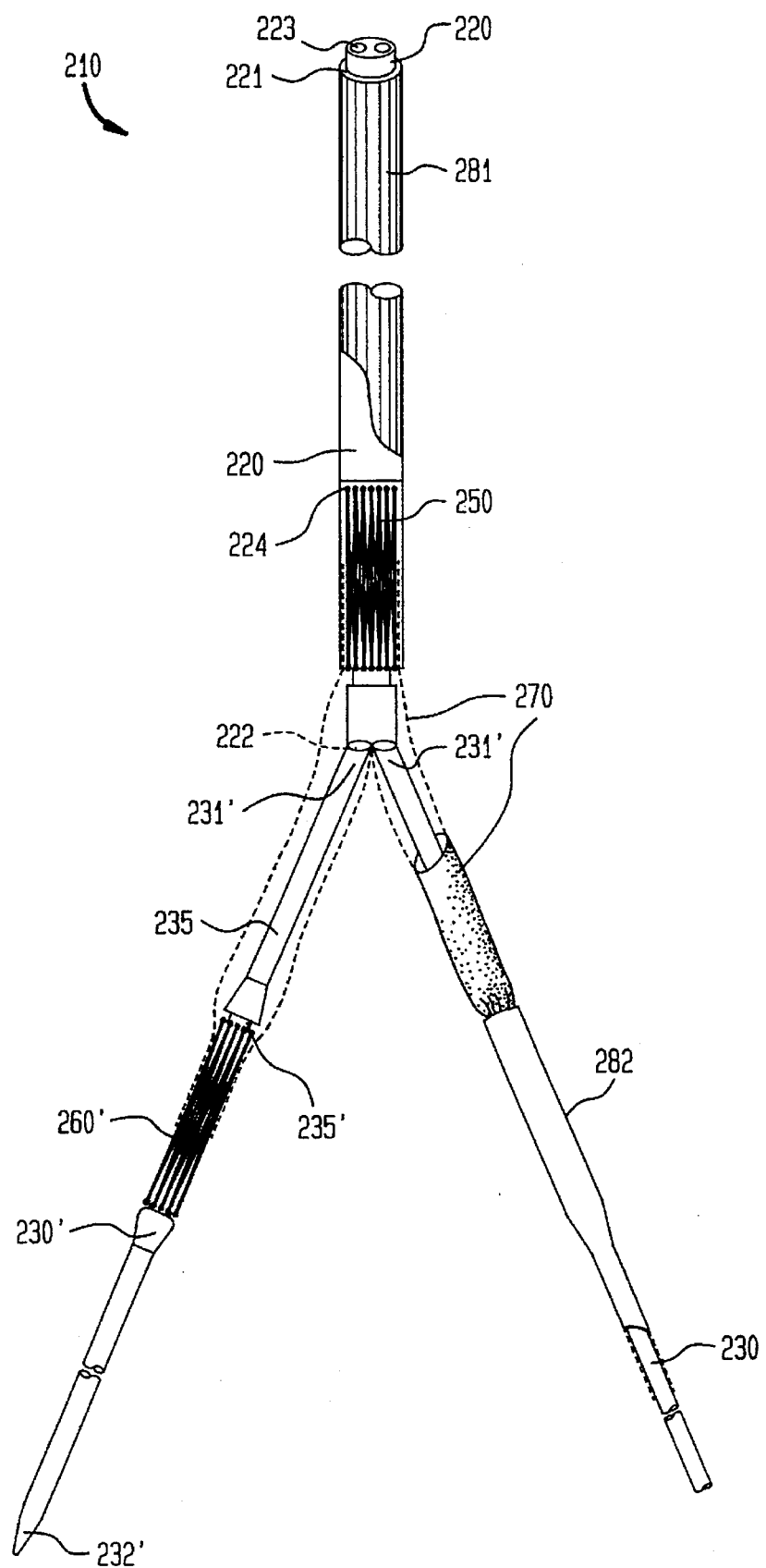
FIG. 5 is a partial cross-section of a mandril assembly, graft and sheath for a fixed length graft.

The above-described assembly 10 of FIG. 1 may be used with either fixed or variable sized grafts. FIG. 5 illustrates another embodiment using an assembly which is particularly adapted for introducing grafts of a fixed length. Because it is not necessary to stretch a fixed-size graft, lower mandrils 230, 230' are permanently attached to and/or integral with the distal portion 222 of the upper mandril 220. In this embodiment, as in any embodiment which utilizes distal or lower mandrils 230, 230' which do not need to be rotated for removal, it is possible to eliminate the use of housing members 34, 34' by building recess 235' directly into the lower mandrils to retain the iliac stent 260'. When the sheaths 281, 282, 282' are withdrawn such that the aortic stent 250 and iliac stents 260 are deployed, the entire assembly including the upper and lower mandrils can be withdrawn through the subclavian 1 incision.

As shown in FIGS. 11–12, this latter design of non-detachable lower mandrils is particularly useful in combination with balloon expandable stents. In the case of balloon expandable stents, an air or gas inlet 390, 391, 391' is built into the proximal end of the assembly 310, and these inlets communicate with balloons 300, 301, 301' disposed around the surface of upper mandril 320, and lower mandrils 330, 330', respectively. Balloon-expandable aortic and iliac stents are, in turn, placed around the balloons. When assembly 310 is properly placed near the aneurysm, balloon 300 underneath the balloon expandable stent 350 in the aorta is inflated via inlet 390, thus increasing the size of the aortic stent and locking the proximal end 371 of the graft 370 in place. The balloon expandable iliac stents 360, 360' are then expanded so as to deploy the iliac stents 360, 365 and secure the distal ends of the graft. Thereafter, balloons 300, 301 301' are deflated and the entire mandril assembly 310 is removed through the subclavian 1.

Figure 6:
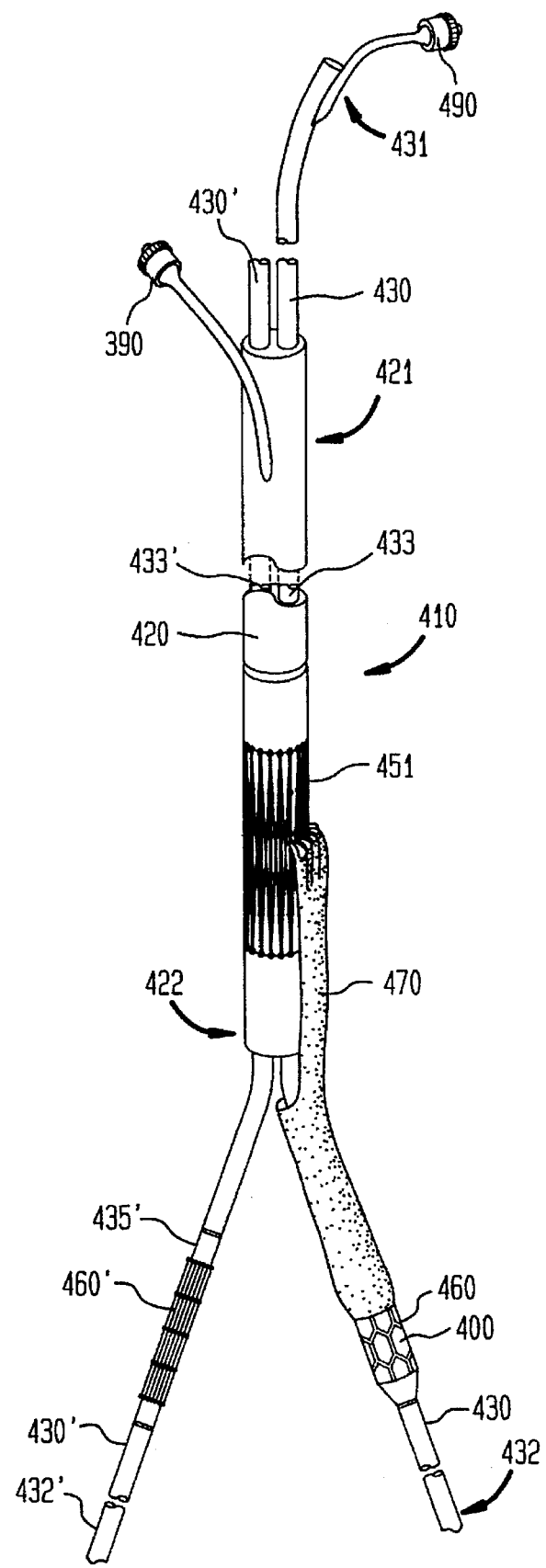
FIG. 6 is a view, in partial cross-section of a bifurcated mandril including balloon expandable stents and slidable lower mandrils.

In yet another preferred embodiment shown in FIG. 6, the lower mandrils 430, 430' of assembly 410 are slidably disposed within and through upper mandril 420. In other words, rather than being in a fixed position with the upper mandril, the lower mandrils slide through the upper mandril. Within upper mandril 420 are two channels 433, 433' extending from proximal end 421 to distal end 422. Lower mandrils 430, 430' extend through these tubes, such that the proximal end 431 of lower mandril 430 extends above the proximal end 421 of upper mandril 420, and distal end 432 of lower mandril 430 extends below the distal end 422 of upper mandril 420. In operation, once the aortic stent 451 is in position and deployed, the individual iliac stents 460, 460' are positioned by pushing and pulling on the proximal ends 431, 432, 432' which extend out of the body of the patient. One advantage of this arrangement is that all of delicate work of carefully positioning the graft can take place in the same end of the patient, i.e., at the proximal end. It may be advisable for this arrangement to include a stop mechanism located a certain distance proximal to the upper end 421 of the upper mandril 420 to ensure that the lower mandrils 430, 430' are not pulled too far so as to rip the stent or withdraw the lower mandrils out of the upper mandril. On the other hand, the stop may be configured to allow for withdrawal of the lower mandrils 430, 430' through the femoral artery 5 when desired. Alternatively, rather than passing the lower mandrils completely through the upper mandrils, it is possible to dispose the proximal end 431 of the lower mandril 430 below the distal end 422 of the upper mandril 420, and then run a rigid wire from the proximal end 431 of the lower mandril 430 up through the channels 433, 433' of the upper mandril 420.

These embodiments can be used either with or without guide wires as previously described. In addition, the device illustrated in FIG. 6 may be particularly useful in performing surgery without the use of incisions in the femoral arteries. Specifically, an incision can be made in the subclavian as previously described and a bifurcated mandril assembly 410 inserted as previously described. The distal ends 432, 432' of the assembly 410, in one embodiment, will be attached to, embedded in or include floatation devices which will allow them to float independently into the two iliac arteries. Alternatively, the distal ends 432 and 432' of the lower mandrils 430 and 430' can be tapered and may include somewhat converging conical tips which form something of a claw shape when positioned in opposition to each other. After mandril assembly 410 is inserted into the subclavian, the lower mandrils could be rotated from the proximal end of the assembly such that the tips 432, 432' diverge to assist in feeding the individual iliac ends of the graft into the respective iliac arteries. In such an arrangement, housings 434 and 434' would be anchored in some way to the body of the upper mandril 420 to prevent the graft 470 from rotating when mandrils 430, 430' are rotated.

In another embodiment, guide wires can be fed into the iliac and femoral arteries as previously described. However, no incisions are made to retrieve same through the legs. Thereafter, the mandril assembly 410 is threaded onto the guide wires 411 and 412 and, generally pushed into position from above. Once the graft 470 has been properly placed and fixed, both the mandril and the guide wires can be removed through the subclavian 1.

FIG. 6 also shows a combination of stent deployment methods. For example, a balloon is used to deploy the iliac stents 460, 460' and a self-expanding stent 70 is used in the aorta. Nearly any combination of stents is possible in accordance with the present invention.

These surgical methods are not limited to only an approach, which introduces the graft through the subclavian. In fact, any entry point or access point which may be provided above the iliac divide and above the junction between the abdominal aorta 3 and the renal arteries 2 can be used. Thus, the axillary artery can be used as can the descending thoracic aorta if, for example, the patient were already on the operating table having open heart or heart bypass surgery. Further, a distal approach may also be used.

Figure 13:
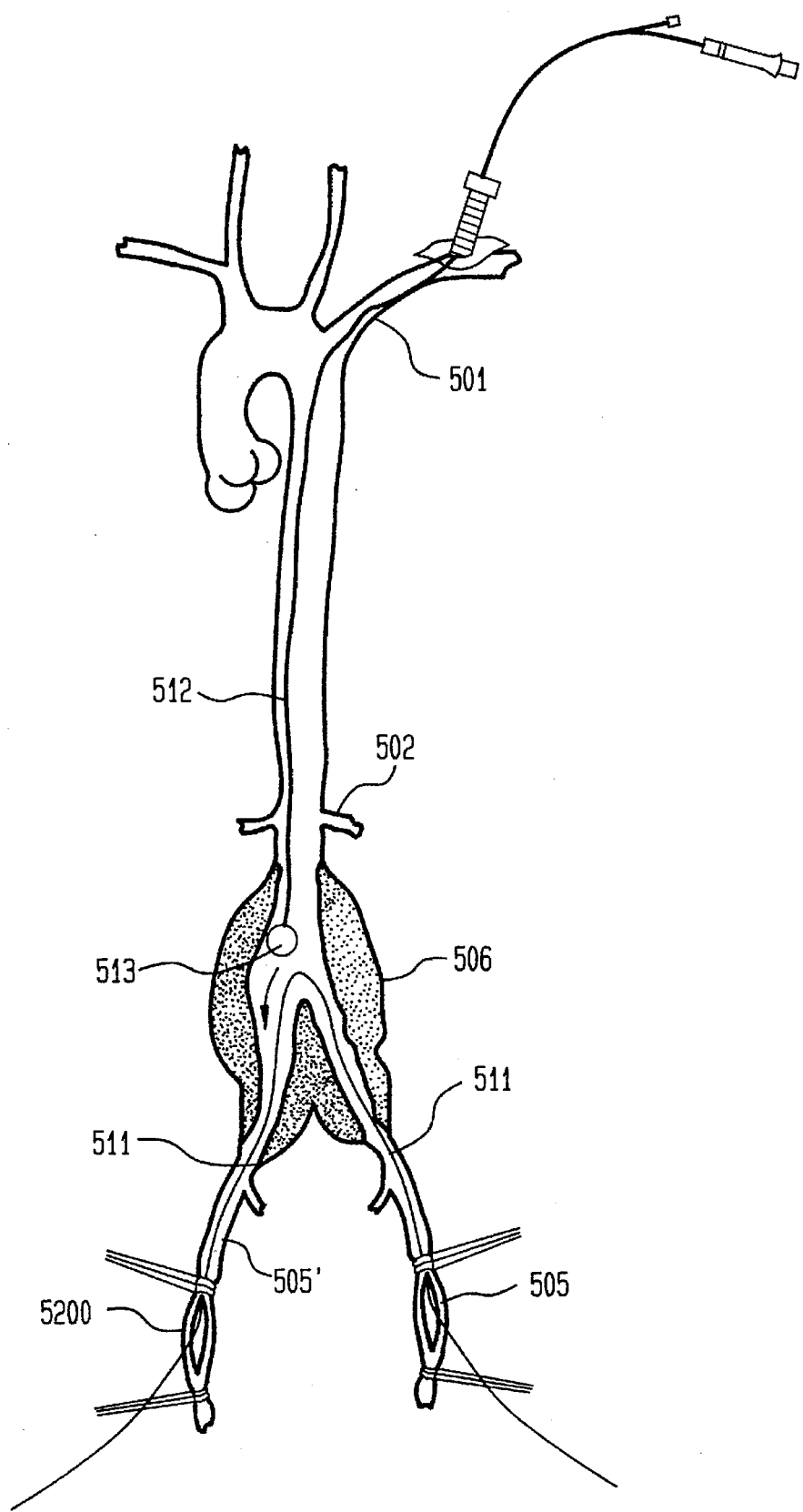
FIG. 13 illustrates another preferred embodiment of threading guide wires for a distal mandril assembly.
Figure 14:
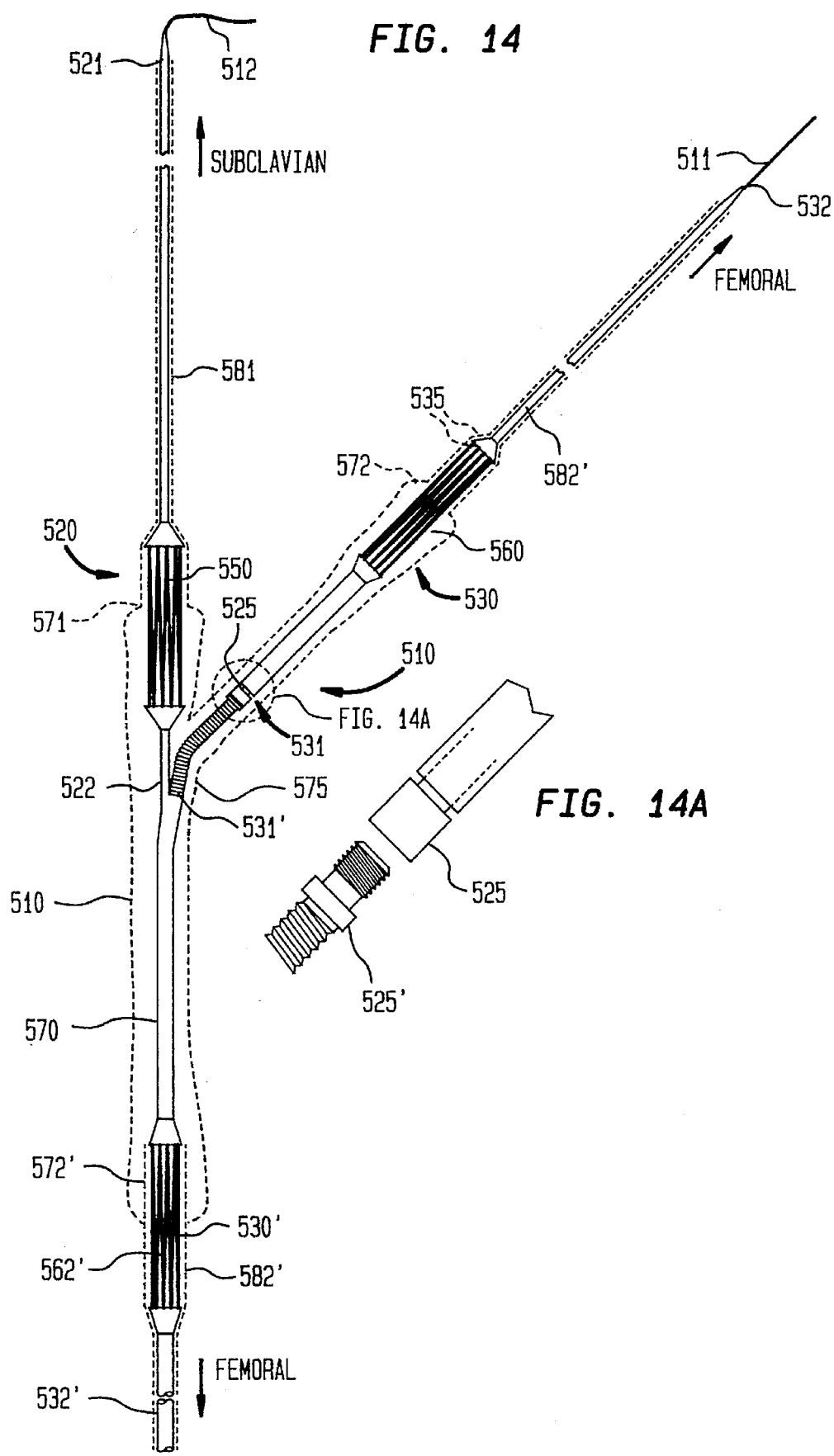
FIG. 14 illustrates a bifurcated mandril assembly for a distal insertion application having self-expandable stents.

As shown in FIGS. 13, 14, mandril assembly 510 is preferably used if a distal approach is selected. While the mandril assembly 510 used in a preferred aspect of the invention is very similar in structure to the mandril assembly 10 previously described, there are some differences. As illustrated in FIG. 14, the graft carrying assembly 510 is placed on the guide wires 511, 512 so that subclavian guide wire 512 is fed through the aortic or proximal end 521 of the upper mandril 510 and through one of lower mandrils 530'. This lower mandril 530' is also referred to as the first iliac end. Thus, the guide wire 512 is fed through the aortic end of the graft 570 and out through the first iliac end thereof. As shown in FIG. 13, lower mandril 530' will remain in the insertion leg and more particularly, in the first iliac artery 505'. The "cross-over" or second guide wire 511 is fed into the "cross-over" or lower mandril 530 through its distal end 532 and again out through the distal end 532' of mandril 530' of the assembly 510. Mandril 530 is also referred to herein as the second iliac end. Thus, the second guide wire 512 is fed though both iliac ends of graft 570.

In most other respects, the distal assembly 510 is substantially the same as the proximal assembly 10 previously described. However, as shown in FIG. 14, the upper assembly 520 may be, and preferably is, integrally formed with lower mandril 530' and is generally not detachable therefrom. Of course, it is possible that upper mandril 520 and lower 530 are detachable through some sort of detachable coupling as previously described. In the configuration illustrated in FIG. 14, upon deployment of the graft, the upper mandril 520 and lower mandril 530' will be removed as a single unit through one of the iliac arteries as further described herein. Otherwise, a detachable coupling device is attached around the proximal end 531' of lower mandril 530' and the upper mandril will be removed through the subclavian with the lower mandril 530' being removed through the first iliac artery.

Lower mandril 530 is preferably attached to the proximal end 531' of the first lower mandril 530'. However, as illustrated in FIG. 14, as upper mandril 520 and lower 530' are essentially one piece, lower mandril 530 may also be considered to be connected to the distal end 522 of upper mandril 520. Preferably, distal mandril 530 is attached to the remainder of the assembly 510 through a detachable coupling member 525 as previously described. In FIG. 14, the detachable coupling includes a threaded receiving member 525 and a threaded male member 525'. Moreover, in a preferred embodiment, a flexible bridge member 575 is disposed to assist assembly 510 and in particular, cross-over mandril 530 in being properly positioned in the second iliac artery and in taking up the substantially "Y" shape required for proper placement of graft 570.

As shown in FIG. 13, in operation, a single wire 512 is run from the subclavian 1 to the leg through which the assembly will be inserted, i.e. common femoral artery 505'. Retrieval of the guide wire 512 is through a transverse arteriotomy as before. Next, BEUAS 5200 is inserted into the common femoral artery 505' along the subclavian guide wire 512. A transverse arteriotomy is performed in the second or opposite common femoral artery 505 and a second guide wire 511 is passed through the BEUAS 5200 and out of the body through the other common femoral artery. Thus, while guide wire 512 runs from the subclavian 1 to the first iliac artery and protrudes therefrom, guide wire 511 runs from the first iliac artery to and through the second iliac artery with one end of guide wire 511 protruding from each of the patient's legs. The reverse can also be accomplished with the end of the cross-over guide wire being snared and brought out through the BEUAS 5200. Guide wires 511 and 512 can be inserted in the reverse order as well.

Next, with the guide wires 511, 512 fed through mandril assembly 510 as described above, both the proximal end 521 of the upper mandril 520 and the distal end 532 of cross-over mandril 530 are advanced through the BEUAS 5200 until the upper end 521 emerges and protrudes from the subclavian 1 and the distal end 532 of the cross-over mandril 530 emerges and protrudes from the femoral artery. As can be seen in FIG. 14, the junction of the upper and lower mandrils are not completely parallel to one another; rather, cross-over lower mandril 530 extends at an obtuse angle from the other lower mandril 530' and at an acute angle to upper mandril 520. This angled rest position enables the assembly to more easily conform to the arterial structure of the patient. Thereafter, the main portion of the assembly 510 including the graft 570 is fed into the first iliac artery 505' with both the aortic end 571 and second iliac end 572 of the graft being advanced ahead of the first iliac 572' end of the graft. Eventually, the aortic stent 550 will be brought into place along guide wire 512 above aneurysm 506 and below the junction with the renal arteries 502. At the same time, the distal assembly 530 will continue along guide wire 511 crossing over the iliac divide, and entering the second iliac artery for placement therein. Finally, the first iliac end of the graft 572' housed on distal mandril 530' will be dragged essentially backwards into place in the iliac artery 505.

Once the graft 570 is in position, only the cross-over lower mandril 530 need be detachable as previously described, although the upper mandril 520 for placing the aortic stent 550 in place may also be detached so as to be removable through the subclavian 501. One possible detachable coupling means is shown in FIG. 14 whereby a portion of detachable coupling means 525 is disposed at the proximal end 531 of cross-over mandril 530 while the other portion 525' is disposed at the proximal end 531' of lower mandril 530'. As described above in connection with other preferred embodiments, the aortic stent 550 is positioned first by manipulating the protruding ends of the mandrils. If a detachable mandril 520 is used for the upper portion of the graft 570, then the upper mandril 520 can be removed through the subclavian artery. Otherwise, mandril 520 is left in place. Next, by manipulating ends 532, 532' of the lower mandrils, the iliac stents 560, 560' are positioned in place. The cross-over mandril is then detached and removed through the femoral artery 505.

It is also possible that the bifurcated mandril in accordance with the present invention be discontinuous. For example, mandril 530 could be totally independent of mandril 520 and mandril 530' essentially eliminating coupling member 525 and bridge 575. The proximal end 531 of distal mandril 530 will therefore be free, albeit disposed within graft 570. In essence, mandril 530 is retained in communication and cooperation with the remaining assembly 510 via graft 570 which is anchored, via stents 550, 560 and 560' as well as sheaths 581, 582 and 582'. Care should be taken to ensure that the distal end 532 of mandril 530 is carefully manipulated so that graft 570 is not twisted upon delivery. Discontinuous mandrils can also be used in the proximal approach as described herein previously.

Figure 15:
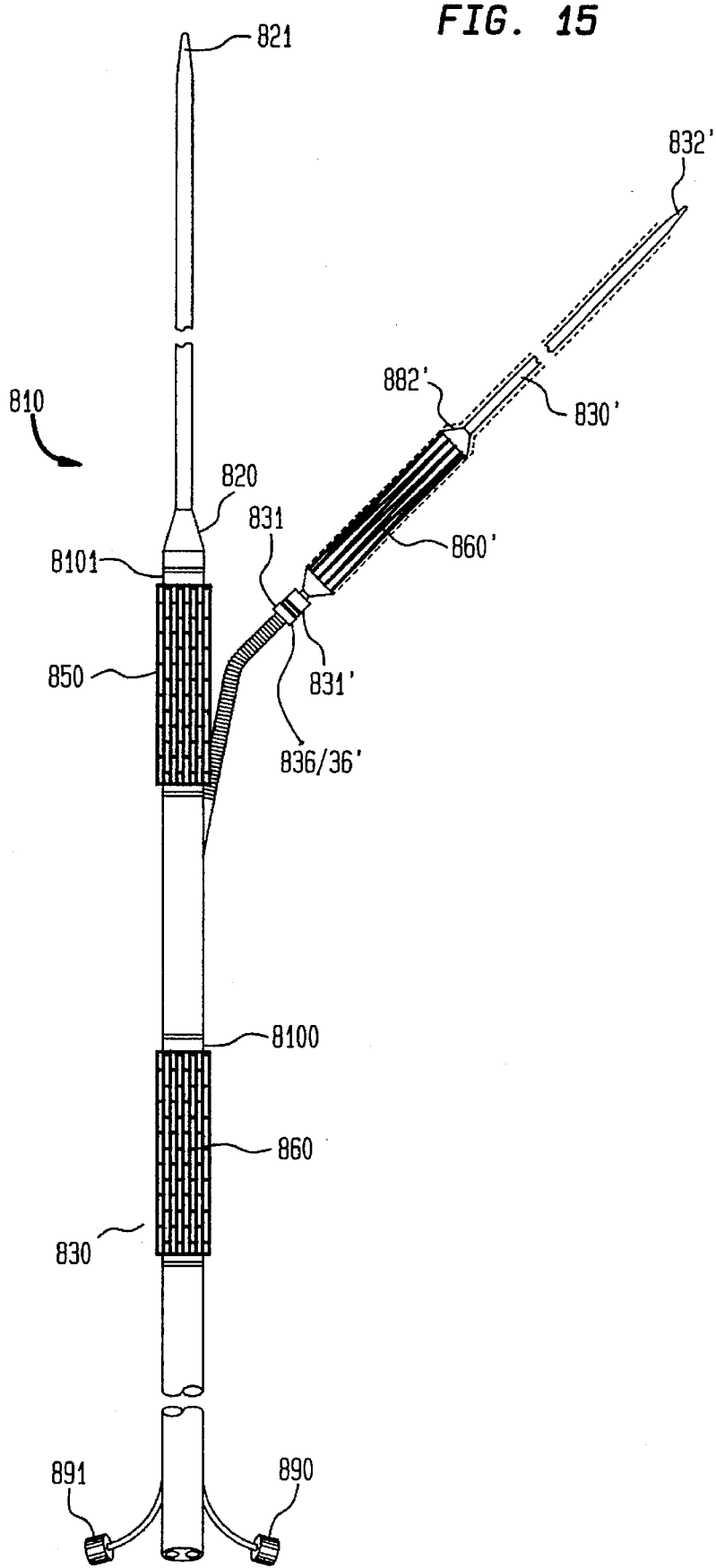
FIG. 15 illustrates a bifurcated mandril for a distal insertion method including both self-expandable and balloon expandable stents.

In an alternate embodiment, it is possible to eliminate the need for an access point in the subclavian artery 1 or any other point above the junction of the abdominal aorta 3 and the renal arteries 2. This may be accomplished by using a relatively shorter guide wire 512 which will dangle within the abdominal aorta or thereabove or by eliminating guide wire 512 completely. Because of the configuration of the distal mandril assembly 510, upper mandril 520 will naturally fall into place in the abdominal aorta and the relative position of aortic stent 550 can be adjusted by manipulating the distal ends 532 and 532' of lower mandrils 530 and 530'. This would be particularly useful when using a device as shown in FIG. 15 which employs balloon expandable stents as there will be no need to employ a sheath around stent 550. If, however, a self expanding stent is used, a pre-split sheath will accommodate withdrawl over the crossover mandril.

It is also possible to use balloon inflatable stents in the distal surgical procedure as well. As shown in FIG. 15, an assembly which is essentially of the same construction as that illustrated in FIG. 14 is provided. However, the aortic stent 850 and the iliac stent 860 which will be deployed in the insertion leg of the patient, in this case, are balloon expandable stents which will be deployed by the input of air or a gas into inlets 890 and 891 respectively to inflate balloons 8100 and 8101 respectively. In using balloon expandable stents and mandrils which can accommodate same, it is not necessary that sheaths be used. However, some form of sheath or outer covering may be desirable to ease insertion and minimize trauma.

It is also possible in accordance with this aspect of the present invention to produce assemblies with combinations of balloon and self-expandable stents. In the embodiment pictured in FIG. 15, the cross-over stent remains as previously described with regard to the embodiment in FIG. 14 utilizing a self-expanding stent 860' and a removable sheath 882'. A self-expanding stent is generally preferred for the cross-over assembly because it is somewhat more complicated to inflate a balloon through the bend in the cross-over mandril 830'. Of course, it could be inflated through a valve disposed at the mandril's distal end 832'. In this embodiment, distal or iliac mandril 830' is withdrawn through the femoral artery of one leg and the remaining assembly including upper mandril 820 and iliac mandril 830 are withdrawn through the femoral artery in the other leg.

Self expanding stents and balloons may also be used in a more direct combination. For example, with reference to FIG. 1 housing 34 may be so constructed as to have a balloon (not shown) within recess 35 disposed underneath or inside of self expanding-iliac stent 60. The balloon can communicate via an air inlet and passage way built into housing 34 or mandril 30 to a gas inlet near the distal end 32 of mandril 30. When sheath 82 is retracted, self expanding stent 60 will expand and be deployed within the iliac artery essentially tacking the iliac end of graft 70 in place. However, it may be desirable to further expand the self expanding stent to insure the degree of engagement between the stent, graft and the iliac wall is sufficient. In that instance, gas may be fed in through the inlet at the distal end of 32 of mandril 30 which will inflate the balloon contained in recess 35. The balloon can then expand and further expand stent 60. Thereafter, the balloon is deflated and surgery progresses as described herein. Such balloons can be used to assist the deployment of the other iliac stent 60' and/or the aortic stent 50 as need be.

As previously described with regard to other constructions, it is not necessary that guide wires be used in accordance with this aspect of the present invention. For example, using an extended mandril or a hybrid mandril as previously described, a long mandril can be fed through the BEUAS, up the femoral and iliac arteries, into the aorta and out through the incision in the subclavian artery. The second mandril, this one attached to the cross-over leg as opposed to the upper portion of the graft, may be fed into the aorta just above the divide of the iliac arteries and snared through the incision in the common femoral artery of the other leg and pulled back therethrough.

Alternatively, in both the subclavian and groin entry protocols, it may be possible to use a device which employs one hollow mandril to accommodate a guide wire running from the subclavian out through one of the common femoral arteries in one of the legs as well as an elongated mahdril attached to one of the bifurcated legs of the assembly carrying one of the bifurcated legs of the graft.

No matter which device as described herein is used and no matter whether the entry approach is through the neck or through the groin, certain attributes of the present invention should be apparent. Most notably, the surgeon has direct control, simultaneously, over each end of the bifurcated graph. This can only be accomplished by the use of a series of entry points or incisions on each side of the afflicted portion of the aorta and iliac arteries and the provision of a device, with or without guide wires, that simultaneously extends out of the body through all three entry points so as to allow a surgeon manipulate every end of the bifurcated graft.

Further, because the present invention preferably allows control over all three ends of the graft (as compared to traditional approaches where one of the iliac ends is usually left to dangle during positioning of the other two ends) and preferably all three ends of the graft and mandril can be directly manipulated from outside of the body, the surgeon will have no trouble getting the both iliac ends into the appropriate position.

In addition, because guide wires in accordance with the present invention only act as tracks for the graft and various delivery assemblies, the wires can be much thinner than those traditionally used in similar operations. For example, wires ranging from a thickness of about 0.18 to about 0.020 may be used. (Currently, the thinnest wire used is about 0.038 gauge wire.)

As described above, nearly any stent may be used in accordance with the present invention. However, one possible self-actuating stent is shown in FIG. 16. The stent is generally cylindrical, and is comprised of two interwoven metal or alloy wires 601 and 603. The wires are made of a material such as Titanium, stainless steel, or known memory materials, which returns to its original shape after reasonable deformation. Wire 601 is a closed loop which zigzags back and forth to define a generally hollow cylindrical boundary, wherein portions of the wire extend from one planar edge of the cylindrical boundary to the other planar edge of the cylindrical boundary, and wherein such portions of the wire are generally at an angle to the planes defined by such planar edges. In other words, wire 601 forms a set of consecutive triangles extending around the surface of a cylinder, with the apex 609 of alternating triangles reaching the top plane 605 of the cylinder and the opposing side of the triangles being open and at the bottom plane 607 of the cylinder.

Stent 600 also includes a second wire 603 having a nearly identical structure to wire 601. However, for every apex 609 of the first wire 601 at the top 605 of the cylinder, there is an apex 611 of the second wire 603 directly opposite apex 609 at the bottom 607 of the cylinder. The two wires 601 and 603 intersect one another midway between the top 605 and bottom 607 planes at a plurality of points 613. Wire 601 remains straight and wire 603 loops around wire 601 in alternating directions forming a loop at midpoint 613. At midpoint 613, wire 601 may have a short portion which is parallel to the top and bottom planes 605, 607 level in order to facilitate the connection. The size of the loop should be sufficient to pass not only wire 601, but also to pass a suture thread. Thus, a surgeon can suture a graft to stent 600 by attaching the graft to the stent at midpoints 613.

The apices 609, 611 preferably do not lie in the same cylindrical surface generally defined by the stent. Rather the apices extend farther outward and away from the center of the cylinder than the rest of the stent. The extended apices in the configuration shown allow for the elimination or minimization of metal fatigue or stress, particularly when compared to stents which may be formed with hard corners. This structure also helps to maintain dynamic tension over a longer periods of time. Rather than crimping the stent at the apices, it is preferable that the apices be somewhat bulbed shaped to aid the performance of the stent as it expands from its contracted position.

As shown in FIG. 17 the balloon expandable universal access sheath or ("BEUAS") 2000 is a universal entry port which may be used in accordance with the surgical methods described herein, as well as any other type of surgical procedure which requires entry into a blood vessel such as an artery or a vein. The use of the BEUAS is certainly not limited to aortic grafting.

BEUAS 2000 comprises a housing 2100 which can be of any shape and cross-section. The generally hollow housing includes an opening at its top into which is placed a diaphragm 2120 (preferably a silicon diaphragm). Diaphragm 2120 preferably contains a central aperture 2140. Disposed within the interior of the housing is a tricuspid valve 2160 (also preferably of silicon or silicon rubber) which, as illustrated in FIG. 17, is a valve comprised of several downward curving or downward extending flaps. Valve 2160 is similar in construction to the tricuspid valve found in the heart. Of course, while a tricuspid valve is illustrated, a two part, four part or other multi-part valve, or its equivalent may also be used. In fact, any valve 2160 or diaphragm 2120 which can perform the functions described herein would be acceptable.

A chamber 2180 is defined between diaphragm 2120 and tricuspid valve 2160. Preferably, access to chamber 2180 is provided via outlet 2200. A second chamber 2220, disposed below tricuspid valve 2160 is also defined. Attached and/or formed integrally with chamber 2220 is a balloon expandable sheath 2260. Sheath 2260 may be composed of a balloon expandable stent having sheath material sutured thereto. However, preferably, the sheath is composed of a weave of cloth and metal material which will expand when a balloon is inserted therein and expanded, just as a balloon expandable stent would. The stent material is disposed longitudinally within the fabric.

BEUAS 2000 cooperates with a balloon insertion device 2300 illustrated in FIG. 18. Device 2300 comprises an air or gas inlet 2310 which feeds air into a handle 2320, down an elongated support rod 2330 and finally into an expandable, non-compliant balloon 2340 disposed around support rod 2330. The balloon 2340 is selected to have a predetermined size and shape upon inflation. Thus balloon 2340 controls the resulting size of the access provided through access 2260 in BEUAS 2000. Preferably, device 2300 is provided with an insertion tip 2350 which will make its insertion into the BEUAS 2000 and into the body easy, without the possibility of damaging various blood vessels.

In operation, device 2300 is inserted into the BEUAS by inserting tip 2350 through aperture 2140 into and through chamber 2180 and into engagement with tricuspid valve 2160. Tricuspid valve 2160 will be pushed away or parted such that the balloon 2340 and stem 2330 of device 2300 can be inserted into expandable sheath 2260. Both devices are then inserted into a blood vessel such as an artery or vein through an incision. Gas is then fed through inlet 2310 through device 2300 and into balloon 2340 whereupon balloon 2340 expands to a predetermined shape and diameter. In so doing, the metal contained within sheath 2260 is deformed and expanded to increase its diameter. The external surface of sheath 2260 generally comes into contact with the walls of the access blood vessel and may stretch that vessels in diameter by up to about 20%. Thereafter, balloon 2340 is deflated and device 2300 is withdrawn from the BEUAS 2000. By removing same, the various members of the tricuspid valve are allowed to return to their original position. The sheath protects the blood vessel and also allows for the straight and uniform insertion and removal of devices, such as the mandril assemblies of the present invention.

In a preferred embodiment, the device 2300 is hollow or is provided with a channel 2360 to allow it to be inserted over a guide wire (not shown).

During surgery, it is not uncommon for there to be some bleeding through the access way or the access incision. By use of the BEUAS, such bleeding can be retarded. Moreover, to the extent that blood collects in chamber 2220 or 2180 that blood can be aspirated or removed using a light suction, cleaned and returned to the body of the patient. The BEUAS may also be secured to the body through use of a suture hold 2240 or other similar structure.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

What I claim is:

1. An apparatus for introducing a second apparatus into the body of a patient and for collecting blood comprising: a hollow sheath having a longitudinal axis extending between a first and second end, a hollow housing defining a housing chamber communicating with said first end of said hollow sheath, first valve means disposed within said housing chamber, said first valve means for allowing insertion of said second apparatus into said housing chamber and through said sheath but substantially retarding blood from exiting said housing chamber, a second valve means disposed within said housing chamber, for allowing passage of said second apparatus from said first chamber into said second chamber, but substantially retarding blood from entering from said second chamber and into said first chamber, said housing chamber thereby comprising a first chamber defined by said housing, said first valve means and said second valve means, said housing chamber further comprising a second chamber defined by said housing, said second valve means and said first end of said sheath, and blood removal means connected to said housing chamber for removing blood from said housing chamber, said blood removal means being disposed within said first chamber.

2. The apparatus of claim 1 wherein said first valve means is a diaphragm having an aperture for passing said second apparatus into said first chamber.

3. The apparatus of claim 1 or 2 wherein said second valve means is a tricuspid valve.

4. The apparatus of claim 1 wherein said blood removal means applies suction to said first chamber.

5. The apparatus of claim 1 wherein said sheath is a balloon-expandable sheath.

* * * * *

UNITED STATES PATENT AND TRADEMARK OFFICE
CERTIFICATE OF CORRECTION

PATENT NO. : 5,662,614
DATED : September 2, 1997
INVENTOR(S) : Edoga

It is certified that error appears in the above-identified patent and that said Letters Patent is hereby corrected as shown below:

Column 1, line 57, after "short" insert --,--.

Column 2, line 25, "patients" should read --patient's--.

Column 2, line 30, "disclosing" should read --discloses--.

Column 2, line 49, after "introducing" insert --a--.

Column 2, line 55, after "means" insert --is--.

Column 3, line 59, before "patient's" insert --the--.

Column 6, line 65, "are" should read --is--.

Column 7, line 58, "and 82." should read --and 82'.--

Column 7, line 60, "patients" should read --patient's--.

Column 8, line 3, after "deploy the stent" insert --,--.

Column 8, line 20, "variety, of" should read --variety of--.

UNITED STATES PATENT AND TRADEMARK OFFICE
CERTIFICATE OF CORRECTION

PATENT NO. : 5,662,614
DATED : September 2, 1997
INVENTOR(S) : Edoga It is certified that error appears in the above-identified patent and that said Letters Patent is hereby corrected as shown below:

Column 8, line 64, "assembly including" should read --assembly, including--.

Column 8, line 64, "mandrils can" should read --mandrils, can--.

Column 9, line 32, "of delicate" should read --of the delicate--.

Column 10, line 57, "fdrther" should read --further--.

Column 12, line 62, "rem.aining" should read --remaining--.

Column 12, line 67, after "FIG. 1" insert --,--.

Column 13, line 2, "expanding-iliac" should read --expanding iliac--.

Column 13, line 35, "mahdril" should read --mandril--.

Column 13, line 48, after "surgeon" insert --to--.

Column 13, line 56, "getting the both" should read --getting both--.

Column 14, line 40, "a longer periods" should read --longer periods--.

Column 15, line 37, "vessels" should read --vessel--.

Signed and Sealed this

Third Day of February, 1998

*Attest:*

BRUCE LEHMAN

*Attesting Officer*  *Commissioner of Patents and Trademarks*